(12) United States Patent
Mederski et al.

(10) Patent No.: US 6,943,179 B2
(45) Date of Patent: Sep. 13, 2005

(54) BIURETHANE DERIVATIVES

(75) Inventors: Werner Mederski, Zwingenberg (DE); Bertram Cezanne, Moerfelden-Walldorf (DE); Dieter Dorsch, Ober-Ramstadt (DE); Christos Tsaklakidis, Weinheim (DE); Johannes Gleitz, Darmstadt (DE); Christopher Barnes, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 59 days.

(21) Appl. No.: 10/472,084

(22) PCT Filed: Feb. 27, 2002

(86) PCT No.: PCT/EP02/02095

§ 371 (c)(1),
(2), (4) Date: Sep. 17, 2003

(87) PCT Pub. No.: WO02/074735

PCT Pub. Date: Sep. 26, 2002

(65) Prior Publication Data

US 2004/0097550 A1 May 20, 2004

(30) Foreign Application Priority Data

Mar. 20, 2001 (DE) .......................... 101 13 402

(51) Int. Cl.$^7$ .................. A61K 31/4412; A61K 31/495; C07D 265/32; C07D 241/08; C07D 281/06
(52) U.S. Cl. .................. 514/327; 514/328; 514/352; 514/357; 514/376; 514/424; 514/425; 514/590; 540/526; 544/166; 544/239; 544/383; 546/220; 546/221; 546/366; 548/229; 548/543; 548/545; 564/35
(58) Field of Search .............................. 564/35; 546/220, 546/221, 366, 332; 544/166, 239, 383; 540/526; 548/229, 543, 545; 514/327, 328, 352, 357, 376, 424, 425, 590

(56) References Cited

U.S. PATENT DOCUMENTS 5,849,732 A  12/1998  Suzuki et al.

FOREIGN PATENT DOCUMENTS

EP  0790240 A  8/1997

OTHER PUBLICATIONS

Zinner, G. et al: "Carbamoylation of hydrazine derivatives" Archiv der Pharmazie (Weinheim, Germany) 1973, 306(1), 35–44, 1973.

Khau, View V. et al "1,3–Dipolar cycloreversion fo a 1, 3, 4–oxadiazoline as a controlled azomethine imine surrogate for pyrazolidine synthesis" Tetrahedron Letter 1996, 37(25), 4323–4326.

Database CA 'online! Chemical Abstracts Service, Columbis, Ohio, US: Utsumi, Naoshi et al : "Production of foamy material" retreived from STN Database accession No. 80:71652 CA.

Cain B F et al : "Potential Antityumour Agents. X. Bisquaternary Salts" Journal of Medicinal Chemistry, Amercian Chemical Society. Washington, US. Bd. 12, Nr.2, Mar. 1969, Seiten 199–206.

*Primary Examiner*—Bernard Dentz
(74) *Attorney, Agent, or Firm*—Millen, White, Zelano, Branigan, P.C.

(57) ABSTRACT

Novel compounds of the formula I in which X, Y, Z, R, $R^1$, $R^2$ and $R^3$ are as defined in Patent Claim 1, are inhibitors of coagulation factor Xa and can be employed for the prophylaxis and/or therapy of tromboembolic diseases and for the treatment of tumors

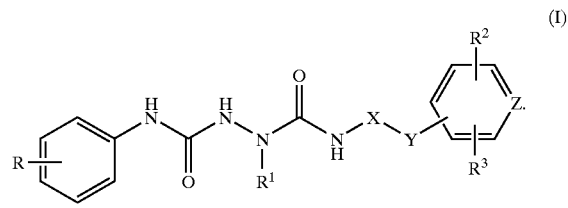

(I)

21 Claims, No Drawings

BIURETHANE DERIVATIVES

This application is a 371 of PCT/EP02/02095 filed Feb. 27, 2002.

The invention relates to compounds of the formula I

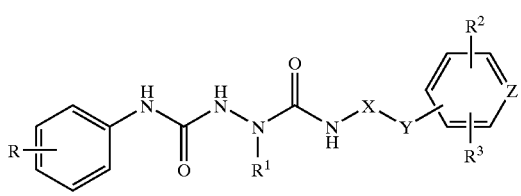

in which
R is H, Hal or CN,
$R^1$ is H, A or $(CH_2)_n$-Ar,
$R^2$ is H or Hal,
$R^3$ is H, phenyl which is unsubstituted or monosubstituted by $SO_2A$, $SO_2NHA$ or $SO_2NH_2$, or Het,
X is $(CH_2)_n$,
Y is absent or is piperidine-1,4-diyl,
Z is CH or N,
Ar is phenyl which is unsubstituted or monosubstituted or disubstituted by Hal, phenyl, A, OH, OA, $NH_2$, NHA, $NA_2$, $NO_2$, CN, COOH, COOA, $CONH_2$, CONHA, $CONA_2$, NHCHO, NACHO, NHCOA, NACOA, $NHSO_2A$, $NASO_2A$, CHO, COA, $SO_2NH_2$, $SO_2NHA$ or $SO_2NA_2$,
Het is a monocyclic saturated, unsaturated or aromatic heterocyclic radical having from 1 to 4 N, O and/or S atoms, which may be unsubstituted or monosubstituted or disubstituted by carbonyl oxygen, Hal, A, OH, OA, $NH_2$, NHA, $NA_2$, $NO_2$, CN, COOH, COOA, $CONH_2$, CONHA, $CONA_2$, NHCHO, NACHO, NHCOA, NACOA, $NHSO_2A$, $NASO_2A$, CHO, COA, $SO_2NH_2$, $SO_2NHA$ or $SO_2NA_2$,
A is unbranched or branched alkyl having 1–6 carbon atoms, in which one or two $CH_2$ groups may be replaced by O or S atoms and/or by —CH=CH— groups and/or in addition 1–7H atoms may be replaced by F,
Hal is F, Cl, Br or I,
n is 0, 1 or 2,
and pharmaceutically usable derivatives, solvates and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexia, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 or WO 00/71516. Cyclic guanidines for the treatment of thromboembolic diseases are described, for example, in WO 97/08165. Aromatic heterocyclic compounds having factor Xa-inhibitory activity are disclosed, for example, in WO 96/10022. Substituted N-[(aminoiminomethyl)phenylalkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation. The inhibition of thrombin can be measured, for example, by the method of G. F. Cousins et al. in *Circulation* 1996, 94, 1705–1712.

Inhibition of factor Xa can thus prevent the formation of thrombin.

The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220–223.

The inhibition of factor Xa can be measured, for example, by the method of T. Hara et al. in *Thromb. Haemostas.* 1994, 71, 314–319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73–81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089–12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57–59.

The publications listed below describe an antitumoural action of TF-VII and factor Xa inhibitors for various types of tumour:

K. M. Donnelly et al. in Thromb. Haemost. 1998; 79: 1041–1047;

E. G. Fischer et al. in J. Clin. Invest. 104: 1213–1221 (1999);

B. M. Mueller et al. in J. Clin. Invest. 101: 1372–1378 (1998);

M. E. Bromberg et al. in Thromb. Haemost. 1999; 82: 88–92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexia, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used for diseases in which blood coagulation makes a crucial contribution to the course of the disease or represents a source of secondary pathology, such as, for example, in cancer, including metastasis, inflammatory disorders, including arthritis, and diabetes.

In the treatment of the diseases described, the compounds according to the invention are also employed in combination with other thrombolytically active compounds, such as, for example, with "tissue plasminogen activator" t-PA, modified t-PA, streptokinase or urokinase. The compounds according to the invention are given either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of the compounds of the formula I according to Claim 1 and salts thereof, characterised in that
a compound of the formula II

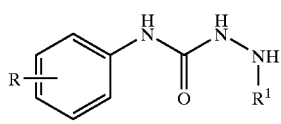

II in which
R and $R^1$ are as defined in Claim 1,
is reacted with a compound of the formula III

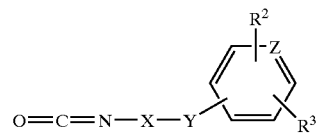

III in which
$R^2$, $R^3$, X, Y and Z are as defined in Claim 1, and/or
a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean, for example, compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61–67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds. For all radicals which occur more than once, such as, for example, A, their meanings are independent of one another.

Above and below, the radicals or parameters R, X, Y, $R^1$, $R^2$ and $R^3$ are as defined under the formula I, unless expressly stated otherwise.

A is alkyl, is unbranched (linear) or branched, and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2-or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A is very particularly preferably alkyl having 1–6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl is preferably, for example, cyclopropyl, cyclobutyl, cyclopentyl, cyclohexyl or cycloheptyl.

Alkylene is preferably methylene, ethylene, propylene, butylene, pentylene or hexylene, furthermore branched alkylene.

—COA(acyl) is preferably acetyl, propionyl, furthermore also butyryl, pentanoyl, hexanoyl or, for example, benzoyl.

Ph is phenyl, Me is methyl, Et is ethyl,

Hal is preferably F, Cl or Br, but also I.

$R^1$ is preferably H, alkyl having 1, 2, 3, 4, 5 or 6 carbon atoms, phenyl or benzyl.

$R^2$ is preferably H, F or Cl.

$R^3$ is preferably mono-$SO_2A$-substituted phenyl or Het.

Ar is, for example, unsubstituted phenyl, naphthyl or biphenyl, furthermore preferably phenyl, naphthyl or biphenyl which is, for example, monosubstituted, disubstituted or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl or aminocarbonyl.

Ar is particularly preferably, for example, phenyl which is unsubstituted or monosubstituted or disubstituted by Hal, A, OH or methoxy.

Het is, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus, for example, also be 2,3-dihydro-2-, -3-, 4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, 4-, -5-, -6-, -7- or -8-isoquinolyl, 2-, 3-, 5-, 6-, 7- or 8- 3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

Het is preferably a monocyclic saturated or unsaturated heterocyclic radical having 1 to 2N and/or O atoms, which may be unsubstituted or monosubstituted or disubstituted by carbonyl oxygen, OH or OA.

Het is, in particular, a monocyclic saturated, unsaturated or aromatic heterocyclic radical having 1 to 2 N and/or O atoms which is monosubstituted or disubstituted by carbonyl oxygen. Het is particularly preferably, for example, pyridyl, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl or 2-methoxy-6-oxopiperazin-1-yl.

The compounds of the formula I may have one or more chiral centres and therefore occur in various stereoisomeric forms. The formula I covers all these forms.

Accordingly, the invention relates in particular to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail are as defined under the formula I, but in which in Ia $R^1$ is $(CH_2)_n Ar$;

in Ib $R^1$ is $(CH_2)_n Ar$ and

Ar is phenyl which is unsubstituted or monosubstituted by Hal;

in Ic $R^1$ is $(CH_2)_n Ar$,

Ar is phenyl which is unsubstituted or monosubstituted by Hal, $R^2$ is H;

in Id $R^1$ is $(CH_2)_n Ar$,

Ar is phenyl which is unsubstituted or monosubstituted by Hal, $R^2$ is H;

$R^3$ is phenyl which is monosubstituted by $SO_2A$ or $SO_2NH_2$, or Het;

in Ie $R^1$ is $(CH_2)_n Ar$,

Ar is phenyl which is unsubstituted or monosubstituted by Hal, $R^2$ is H, $R^3$ is phenyl which is monosubstituted by $SO_2A$ or $SO_2NH_2$, or Het, Het is a monocyclic, saturated or unsaturated heterocyclic radical having 1 to 2 N and/or O atoms, which may be unsubstituted or monosubstituted or disubstituted by carbonyl oxygen, OH or OA;

in If $R^1$ is $(CH_2)_n Ar$,

Ar is phenyl which is unsubstituted or monosubstituted by Hal, $R^2$ is H, $R^3$ is phenyl which is monosubstituted by $SO_2A$ or $SO_2NH_2$, or Het, Het is pyridyl, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl, 2-hydroxy-6-oxopiperazin-1-yl or 2-methoxy-6-oxopiperazin-1-yl;

in Ig Het is a monocyclic, saturated or unsaturated heterocyclic radical having 1 to 2 N and/or O atoms, which may be unsubstituted or monosubstituted or disubstituted by carbonyl oxygen, OH or OA;

and pharmaceutically tolerated salts, solvates and stereoisomers thereof.

The compounds of the formula I and also the starting materials for the preparation are, in addition, prepared by methods known per se, as described in the literature (for example in the standard works, such as Houben-Weyl, Methoden der organischen Chemie [methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Compounds of the formula I can preferably be obtained by reacting compounds of the formula II with compounds of the formula III.

The reaction is generally carried out in an inert solvent. Depending on the conditions used, the reaction time is between a few minutes and 14 days, and the reaction temperature is between about 0° and 150°, normally between 20° and 130°.

Examples of suitable inert solvents are water, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds of the formulae II and III are generally known. If they are novel, they can, however, be prepared by methods known per se. Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methaneor ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline) or N-benzenesulfonylproline), or the various optically active camphorsulfonic acids. Also advantage is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Examples of suitable eluents for this purpose are aqueous or alcoholic solvent mixtures, such as, for example, hexane/isopropanol/acetonitrile, for example in the ratio 82:15:3.

The invention furthermore relates to the use of compounds of the formula I and/or physiologically acceptable salts f thereof or the preparation of pharmaceutical preparations, in particular by non-chemical methods. They can be converted here into a suitable dosage form together with at least one solid, liquid and/or semiliquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

The invention furthermore relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and physiologically acceptable salts thereof can be used for combating thromboembolic diseases, such as thrombosis, myocardial infarction, arteriosclerosis, inflammation, apoplexia, angina pectoris, restenosis after angioplasty, claudicatio intermittens, tumours, tumour diseases and/or tumour metastases.

In general, the substances according to the invention are preferably administered in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates and stereoisomers thereof, including mixtures thereof in all ratios,
for the preparation of a medicament for the treatment of thrombosis, myocardial infarction, arteriosclerosis, inflammation, apoplexia, angina pectoris, restenosis after angioplasty, claudicatio intermittens, tumours, tumour diseases and/or tumour metastases,
in combination with at least one further medicament active ingredient.

Above and below, all temperatures are given in ° C. In the following examples, 'conventional work-up' means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron ionisation) M+
FAB (fast atom bombardment) (M+H)+
ESI (electrospray ionisation) (M+H)+ (unless specified otherwise)

EXAMPLES
Compounds of the Formula I

TABLE 1

I

| No. | R | $R^1$ | X | Y | Z | $R^3$ | m.p. [° C.] |
|---|---|---|---|---|---|---|---|
| 1 | 4-Cl | Ph | — | — | CH | 2-Oxo-piperidin-1-yl | 165–170 |
| 2 | 4-Cl | 4-Cl—Ph | — | — | CH | 2-Oxo-piperidin-1-yl | 170–175 |
| 3 | 4-Cl | Ph | — | — | CH | 2-Methylsulfonyl-phenyl | >250 |
| 4 | 4-Cl | Ph | — | — | CH | 2,6-Dioxo-piperazin-1-yl | |
| 5 | 4-Cl | Ph | — | — | CH | 2-Oxo-piperazin-1-yl | |
| 6 | 4-Cl | Ph | — | — | CH | 2-Oxo-1H-pyridin-1-yl, | |
| 7 | 4-Cl | Ph | — | — | CH | 2-Hydroxy-6-oxo-piperazin-1-yl | |
| 8 | 4-Cl | Ph | — | — | CH | 2-Methoxy-6-oxo-piperazin-1-yl | |
| 9 | 4-CN | Ph | — | — | CH | 2-Oxo-piperazin-1-yl | |
| 10 | 4-CN | Ph | — | — | CH | 2-Oxo-piperidin-1-yl | |
| 11 | 4-CN | Ph | — | — | CH | 3-Oxo-morpholin-4-yl | |
| 12 | 4-Cl | Ph | — | — | CH | 3-Oxo-morpholin-4-yl | |
| 13 | 4-Cl | Ph | $CH_2$ | — | CH | 2-Oxo-1H-pyridin-1-yl, | |
| 14 | 4-Cl | Ph | $CH_2$ | — | CH | 2-Oxo-piperidin-1-yl | |
| 15 | 4-Cl | Ph | $CH_2$ | "1" | N | H | |
| 16 | 4-Cl | Ph | — | — | CH | 2-Oxo-azepan-1-yl | |

Ph = phenyl; $R^2$ = H;

"1" = 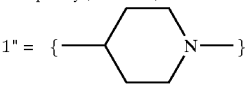

Example 1
Preparation of Compound No. 1
N-(4-Chlorophenylaminocarbonyl)-N'-[4-(2-oxo-1-piperidyl)phenylaminocarbonyl]-N'-phenylhydrazine 1.1 A solution of 15.35 g of 4-chlorophenyl isocyanate in 50 ml of THF is added to a solution of 9.83 g of phenylhydrazine in 100 ml of THF under a nitrogen atmosphere, and the mixture is refluxed for 2 hours. Conventional work-up gives 25.1 g of N-(4-chlorophenylaminocarbonyl)-N'-phenylhydrazine("AA"), El 277, m.p. 187–189.

1.2 0.032 ml of trichloromethyl chloroformate is added under a nitrogen atmosphere to a solution of 50 mg of 1-(4-aminophenyl)piperidin-2-one (prepared from 1-(4-nitrophenyl)piperidin-2-one by hydrogenation using Raney nickel as catalyst) in 5 ml of THF, and the mixture is subsequently refluxed for 1.5 hours, giving 1-(4-isocyanatophenyl)piperidin-2-one ("AB").

1.3 78.4 mg of "AA" are added to the solution comprising "AB", and the mixture is refluxed for 2 hours and subjected to conventional workup, giving 105 mg of N-(4-chlorophenylaminocarbonyl)-N'-[4-(2-oxo-1-piperidyl)phenylaminocarbonyl]-N'-phenylhydrazine, El 478, m.p. 165–170° (decomposition).

The compounds shown in Table 1 are prepared analogously.

Pharmacological Data
Affinity to Receptors

TABLE 2

| No. | m.p. [° C.] | FXa-IC$_{50}$ [nM/L] | TF/FVIIa-IC$_{50}$ [nM/L] |
|---|---|---|---|
| 1 | 165–170 | 180.0 | 91.0 |
| 2 | 170–175 | 670.0 | 340.0 |
| 3 | >250 | 390.0 | 190.0 |

The following examples relate to pharmaceutical preparations:

Example A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

What is claimed is:

1. A compound of the formula I

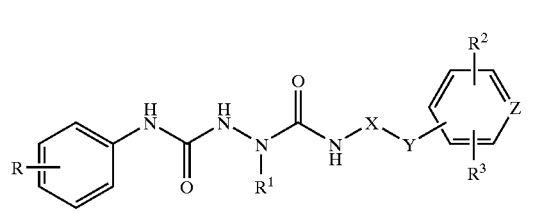

wherein

R is H, Hal or CN,

R$^1$ is H, A or (CH$_2$)$_n$-Ar,

R$^2$ is H or Hal,

R$^3$ is phenyl which is unsubstituted or monosubstituted by SO$_2$A, SO$_2$NHA or SO$_2$NH$_2$, or Het, X is (CH$_2$)$_n$, Y is absent, Z is CH or N, Ar is phenyl which is unsubstituted or monosubstituted or disubstituted by Hal, phenyl, A, OH, OA, NH$_2$, NHA, NA$_2$, NO$_2$, CN, COOH, COOA, CONH$_2$, CONHA, CONA$_2$, NHCHO, NACHO, NHCOA, NACOA, NHSO$_2$A, NASO$_2$A, CHO, COA, SO$_2$NH$_2$, SO$_2$NHA or SO$_2$NA$_2$, Het is a monocyclic saturated, unsaturated or aromatic heterocyclic radical having from 1 to 4 N, O and/or S atoms, which may be unsubstituted, monosubstituted or disubstituted by carbonyl oxygen, Hal, A, OH, OA, NH$_2$, NHA, NA$_2$, NO$_2$, CN, COOH, COOA, CONH$_2$, CONHA, CONA$_2$, NHCHO, NACHO, NHCOA, NACOA, NHSO$_2$A, NASO$_2$A, CHO, COA, SO$_2$NH$_2$, SO$_2$NHA or SO$_2$NA$_2$, A is unbranched or branched alkyl having 1–6 carbon atoms, in which one or two CH$_2$ groups may be replaced by O or S atoms and/or by —CH═CH— groups and/or in addition 1–7 H atoms may be replaced by F, Hal is F, Cl, Br or I, n is 0, 1 or 2, or a pharmaceutically acceptable salt solvate, stereoisomer or a mixture thereof.

2. A compound according to claim 1, wherein $R^2$ is H.

3. A compound according to claim 1, wherein $R^1$ is $(CH_2)_nAr$.

4. A compound according to claim 1, wherein
$R^1$ is $(CH_2)_nAr$, and
Ar is phenyl which is unsubstituted or monosubstituted by Hal.

5. A compound according to claim 1, wherein
$R^1$ is $(CH_2)_nAr$,
Ar is phenyl which is unsubstituted or monosubstituted by Hal, and
$R^2$ is H.

6. A compound according to claim 1, wherein
$R^1$ is $(CH_2)_nAr$,
Ar is phenyl which is unsubstituted or monosubstituted by Hal,
$R^2$ is H, and
$R^3$ is phenyl which is monosubstituted by $SO_2A$, $SO_2NH_2$, or Het.

7. A compound according to claim 1, wherein
$R^1$ is $(CH_2)_nAr$,
Ar is phenyl which is unsubstituted or monosubstituted by Hal,
$R^2$ is H,
$R^3$ is phenyl which is monosubstituted by $SO_2A$, $SO_2NH_2$, or Het, and
Het is a monocyclic, saturated or unsaturated heterocyclic radical having 1 or 2 N and/or O atoms, which may be unsubstituted, monosubstituted or disubstituted by carbonyl oxygen, OH or OA.

8. A compound according to claim 1, wherein
$R^1$ is $(CH_2)_nAr$,
Ar is phenyl which is unsubstituted or monosubstituted by Hal,
$R^2$ is H,
$R^3$ is phenyl which is monosubstituted by $SO_2A$, $SO_2NH_2$, or Het,
Het is pyridyl, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl, 2-hydroxy-6-oxopiperazin-1-yl or 2-methoxy-6-oxopiperazin-1-yl.

9. A compound according to claim 1, wherein Het is a monocyclic, saturated or unsaturated heterocyclic radical having 1 or 2 N and/or O atoms, which may be unsubstituted, monosubstituted or disubstituted by carbonyl oxygen, OH or OA.

10. A compound according to claim 1, selected from the group consisting of
N-(4-chlorophenylaminocarbonyl)-N'-[4-(2-oxo-1-piperidyl)phenylaminocarbonyl]-N'-phenylhydrazine,
N-(4-chlorophenylaminocarbonyl)-N'-[4-(2-oxo-1-piperidyl)phenylaminocarbonyl]-N'-4-chlorophenylhydrazine,
N-(4-chlorophenylaminocarbonyl)-N'-[4-(2-methylsulfonylphenyl)phenylaminocarbonyl]-N'-phenylhydrazine,
N-(4-chlorophenylaminocarbonyl)-N'-[4-(2,6-dioxo-1-piperazinyl)phenylaminocarbonyl]-N'-phenylhydrazine,
N-(4-chlorophenylaminocarbonyl)-N'-[4-(2-oxo-1-piperazinyl)phenylaminocarbonyl]-N'-phenylhydrazine,
N-(4-chlorophenylaminocarbonyl)-N'-[4-(2-oxo-1H-pyridin-1-yl)phenylaminocarbonyl]-N'-phenylhydrazine,
N-(4-chlorophenylaminocarbonyl)-N'-[4-(2-hydroxy-6-oxo-1-piperazinyl)phenylaminocarbonyl]-N'-phenylhydrazine,
N-(4-chlorophenylaminocarbonyl)-N'-[4-(2-methoxy-6-oxo-1-piperazinyl)phenylaminocarbonyl]-N'-phenylhydrazine,
N-(4-cyanophenylaminocarbonyl)-N'-[4-(2-oxo-1-piperazinyl)phenylaminocarbonyl]-N'-phenylhydrazine,
N-(4-cyanophenylaminocarbonyl)-N'-[4-(2-oxo-1-piperidyl)phenylaminocarbonyl]-N'-phenylhydrazine,
N-(4-cyanophenylaminocarbonyl)-N'-[4-(3-oxomorpholin-4-yl)phenylaminocarbonyl]-N'-phenylhydrazine,
N-(4-chlorophenylaminocarbonyl)-N'-[4-(3-oxomorpholin-4-yl)phenylaminocarbonyl]-N'-phenylhydrazine,
N-(4-chlorophenylaminocarbonyl)-N'-[4-(2-oxo-1H-pyridin-1-yl)phenylmethylaminocarbonyl]-N'-phenylhydrazine,
N-(4-chlorophenylaminocarbonyl)-N'-[4-(2-oxo-1-piperidyl)phenylmethylaminocarbonyl]-N'-phenylhydrazine,
and their pharmaceutically acceptable salts, solvates and stereoisomers, including their mixtures in all ratios.

11. A process for preparing a compound of the formula I according to claim 1 or a pharmaceutically tolerated salt or solvate, comprising reacting
a compound of the formula II

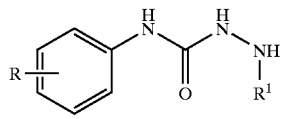

II with a compound of the formula III

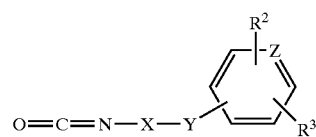

III and optionally converting
a base or acid of the formula I into one of its salts.

12. A compound of the formula I according to claim 1 as an inhibitor of coagulation factor Xa.

13. A compound of the formula I according to claim 1 as an inhibitor of coagulation factor VIIa.

14. A pharmaceutical composition comprising at least one compound of the formula I according to claim 1 and/or a pharmaceutically acceptable salt, solvate, or stereoisomer, including a mixture thereof, and optionally excipient and/or an assistant.

15. A pharmaceutical composition comprising at least one compound of the formula I according to claim 1 and/or the pharmaceutically usable salt, solvate, or stereoisomer, including a mixture thereof in all ratios, and at least one further pharmaceutical active ingredient.

16. A pharmaceutical composition for the treatment of thrombosis, myocardial infarction, arteriosclerosis, inflammation, apoplexia, angina pectoris, restenosis after angioplasty, claudicatio intermittens, tumours, tumour diseases and/or tumour metastases, comprising a compound according to claim 1 and/or a physiologically acceptable salt or solvate and a pharmaceutically acceptable carrier.

17. A kit comprising separate packs of
   (a) an effective amount of a compound of the formula I according to claim 1 and/or a pharmaceutically usable salt, solvate, or stereoisomer, including a mixture thereof in all ratios, and
   (b) an effective amount of a further pharmaceutical active ingredient.

18. A pharmaceutical composition for the treatment of thrombosis, myocardial infarction, arteriosclerosis, inflammation, apoplexia, angina pectoris, restenosis after angioplasty, claudicatio intermittens, tumours, tumour diseases and/or tumour metastases, comprising a compound according to claim 1 and/or a pharmaceutically acceptable derivative, solvate or stereoisomer in combination with at least one further pharmaceutical active ingredient.

19. A pharmaceutical acceptable solvate, stereoisomer, or a mixture thereof, of a compound according to claim 1.

20. A method of treating thrombosis, myocardial infarction, arteriosclerosis, inflammation, apoplexia, angina pectoris, restenosis after angioplasty, claudicatio intermittens, tumours, tumour diseases and/or tumour metastases, comprising administering an effective amount of a compound according to claim 1 to a patient in need thereof.

21. A compound of the formula I

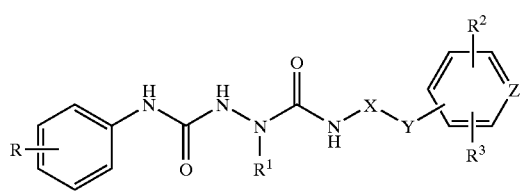

I wherein

R is H, Hal or CN $R^1$ is H, A or $(CH_2)_{n\text{-}Ar}$, $R^2$ is H or Hal, $R^3$ is phenyl which is unsubstituted or monosubstituted by $SO_2A$, $SO_2NHA$ or $SO_2NH_2$, or Het, X is $(CH_2)_n$, Y is absent, Z is CH or N, Ar is phenyl which is unsubstituted, monosubstituted or disubstituted by Hal, phenyl, A, OH, OA, $NH_2$, NHA, $NA_2$, $NO_2$, CN, COOH, COOA, $CONH_2$, CONHA, $CONA_2$, NHCHO, NACHO, NHCOA, NACOA, $NHSO_2A$, $NASO_2A$, CHO, COA, $SO_2NH_2$, $SO_2NHA$ or $SO_2NA_2$, Het is a monocyclic saturated, unsaturated or aromatic heterocyclic radial having from 1 to 4 N, O and/or S atoms, which may be unsubstituted, monosubstituted or disubstituted by carbonyl oxygen, Hal, A, OH, OA, $NH_2$, NHA, $NA_2$, $NO_2$, CN, COOH, COOA, $CONH_2$, CONHA, $CONA_2$, NHCHO, NACHO, NHCOA, NACOA, $NHSO_2A$, $NASO_2A$, CHO, COA, $SO_2NH_2$, $SO_2NHA$ or $SO_2NA_2$, A is unbranched or branched alkyl having 1–6 carbon atoms, in which one or two $CH_2$ groups may be replaced by O or S atoms and/or by —CH=CH— groups and/or in addition 1–7 H atoms may be replaced by F, Hal is F, Cl, Br or I, n is 0, 2 or 2, or a pharmaceutically acceptable derivative, solvate, stereoisomer or a mixture thereof.

* * * * *